US012616482B1

(12) United States Patent
Pedicini

(10) Patent No.: US 12,616,482 B1
(45) Date of Patent: May 5, 2026

(54) ORTHOPEDIC IMPACTOR

(71) Applicant: Fidelis Partners, LLC, Cheyenne, WY (US)

(72) Inventor: Christopher Pedicini, Brentwood, TN (US)

(73) Assignee: Fidelis Partners, LLC, Cheyenne, WY (US)

( * ) Notice: Subject to any disclaimer, the term of this patent is extended or adjusted under 35 U.S.C. 154(b) by 0 days.

(21) Appl. No.: 19/338,475

(22) Filed: Sep. 24, 2025

Related U.S. Application Data

(60) Provisional application No. 63/863,882, filed on Aug. 14, 2025.

(51) Int. Cl.
    *A61B 17/92*     (2006.01)
    *A61B 17/16*     (2006.01)

(52) U.S. Cl.
    CPC ...... *A61B 17/1657* (2013.01); *A61B 17/1628* (2013.01)

(58) Field of Classification Search
    CPC ................................... A61B 17/92–2017/928
    See application file for complete search history.

(56) References Cited

U.S. PATENT DOCUMENTS

| | | | |
|---|---|---|---|
| 6,520,266 B2 * | 2/2003 | Bongers-Ambrosius | ................... B25D 11/12 173/2 |
| 6,868,918 B2 | 3/2005 | Shinohara | |
| 10,342,591 B2 | 7/2019 | Pedicini | |

| | | | |
|---|---|---|---|
| 11,013,503 B2 * | 5/2021 | Pedicini | ............... A61B 17/025 |
| 11,696,770 B2 | 7/2023 | Pedicini | |
| 11,779,469 B2 * | 10/2023 | Hosseini | ............... A61F 2/4603 606/99 |
| 12,004,793 B2 | 6/2024 | Levy | |
| 12,029,406 B2 * | 7/2024 | Pedicini | ............... A61B 17/025 |
| 12,064,158 B2 | 8/2024 | Marinkovich | |
| 12,070,256 B2 | 8/2024 | Slocum et al. | |
| 12,121,279 B2 * | 10/2024 | Pedicini | ................. A61B 17/92 |
| 12,290,300 B1 * | 5/2025 | Pedicini | ................. A61B 17/92 |
| 12,440,224 B1 * | 10/2025 | Pedicini | ............ A61B 17/1631 |
| 2008/0190988 A1 * | 8/2008 | Pedicini | ................... B25C 1/04 137/540 |

(Continued)

OTHER PUBLICATIONS

International Search Report and Written Opinion issued Aug. 12, 2025 in related International Patent Application No. PCT/US2025/035879, 6 pages.

*Primary Examiner* — Zade Coley
(74) *Attorney, Agent, or Firm* — XSENSUS LLP

(57) ABSTRACT

An orthopedic impactor may include a motor operable to generate first rotational motion and second rotational motion, a linear motion converter operatively coupled to the motor to convert the first rotational motion into first linear motion and the second rotational motion into second linear motion, an anvil including at least one impact surface, and a thrown mass having a first position located a distance from the at least one impact surface. The thrown mass may accelerate, responsive to the first linear motion and away from the first position, toward the anvil to impact the at least one impact surface with a first kinetic energy and impart a linear impact force on the anvil. The thrown mass may return, responsive to the second linear motion and toward the first position, with a second kinetic energy that is less than the first kinetic energy.

19 Claims, 1 Drawing Sheet

100

(56)  References Cited

U.S. PATENT DOCUMENTS

| 2011/0064978 | A1  |  3/2011 | McGahan et al. |
| 2016/0199199 | A1  |  7/2016 | Pedicini |
| 2017/0020536 | A1* |  1/2017 | Johnson ................. A61B 17/92 |
| 2017/0100829 | A1* |  4/2017 | Pedicini .................. B25C 1/047 |
| 2018/0055518 | A1  |  3/2018 | Pedicini |
| 2018/0055552 | A1* |  3/2018 | Pedicini ................. A61B 17/92 |
| 2019/0183554 | A1* |  6/2019 | Pedicini ............... B25D 11/108 |
| 2021/0330367 | A1* | 10/2021 | Pedicini ................. A61B 17/92 |
| 2022/0142693 | A1  |  5/2022 | Slocum et al. |
| 2022/0226033 | A1  |  7/2022 | Slocum et al. |
| 2022/0240947 | A1  |  8/2022 | Marinkovich |
| 2022/0273317 | A1  |  9/2022 | Levy |
| 2022/0323134 | A1* | 10/2022 | Lyon ..................... A61B 17/92 |

\* cited by examiner

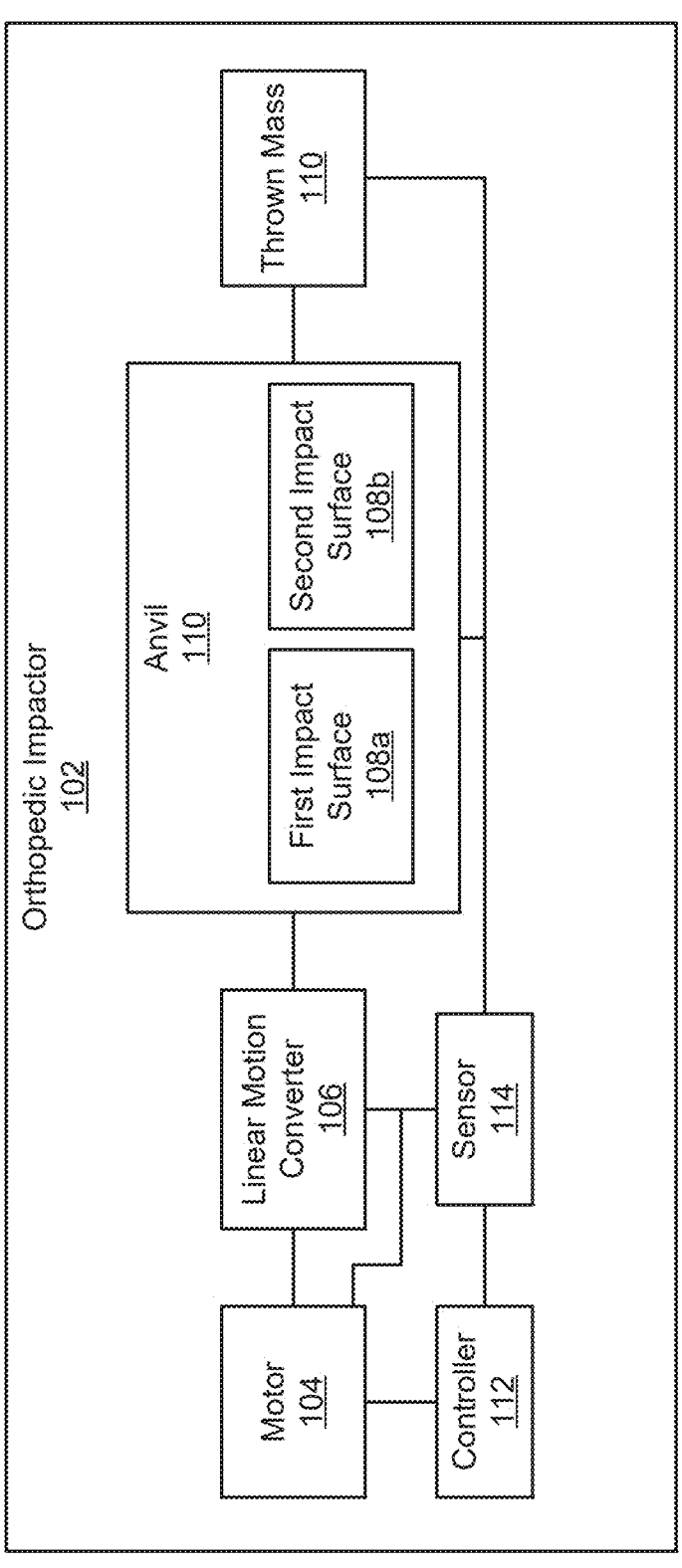

ORTHOPEDIC IMPACTOR

CROSS-REFERENCE TO RELATED APPLICATIONS

This application claims the benefit of U.S. Provisional Application No. 63/863,882, filed Aug. 14, 2025, which is incorporated by reference in its entirety.

BACKGROUND

Impactors are designed to deliver an impact force to a target object or material. The impactors are commonly used in various industries and applications where precise and controlled force is required to perform tasks, such as fastening, shaping, breaking, and/or compacting tasks.

SUMMARY

In some aspects, the techniques described herein relate to an orthopedic impactor, including: a motor operable to generate first rotational motion and second rotational motion, the first rotational motion and the second rotational motion being opposite in direction; a linear motion converter operatively coupled to the motor to convert the first rotational motion into first linear motion and the second rotational motion into second linear motion, the first linear motion and the second linear motion being opposite in direction; an anvil including at least one impact surface; and a thrown mass operatively coupled to the linear motion converter having a first position located a distance from the at least one impact surface, wherein, during an operational cycle of the orthopedic impactor: the thrown mass accelerates, responsive to the first linear motion and away from the first position, toward the anvil to impact the at least one impact surface with a first kinetic energy and impart a linear impact force on the anvil, and the thrown mass returns, responsive to the second linear motion and toward the first position, with a second kinetic energy that is less than the first kinetic energy.

In some aspects, the techniques described herein relate to an orthopedic impactor, including: a motor operable to generate rotational motion; a means for converting the rotational motion to linear motion; an anvil including at least one impact surface; and a thrown mass having a first position located a distance from the at least one impact surface, wherein, during an operational cycle of the orthopedic impactor: the thrown mass accelerates, responsive to the linear motion and away from the first position, toward the anvil to impact the at least one impact surface with a first kinetic energy and impart a linear impact force on the anvil, and the thrown mass returns, responsive to the linear motion and toward the first position, with a second kinetic energy that is less than the first kinetic energy.

In some aspects, the techniques described herein relate to an orthopedic impactor, including: a motor configured to generate rotational motion; a linear motion converter operatively coupled to the motor and configured to convert the rotational motion into linear motion; a thrown mass operatively coupled to the linear motion converter and movable between a ready position and an impact position; an anvil including at least one impact surface positioned to receive impact from the thrown mass; and a controller configured to: control the motor to accelerate the thrown mass from the ready position toward the impact position with a first kinetic energy magnitude, and control the motor to return the thrown mass from the impact position toward the ready position with a second kinetic energy magnitude that is reduced relative to the first kinetic energy magnitude.

BRIEF DESCRIPTION OF THE DRAWINGS

The FIGURE is a diagram of an example associated with an orthopedic impactor.

DETAILED DESCRIPTION OF EXAMPLE EMBODIMENTS

The following detailed description of example implementations refers to the accompanying drawings. The same reference numbers in different drawings may identify the same or similar elements.

In the field of orthopedics, prosthetic devices, such as artificial joints, are often implanted or seated in a bone cavity of a patient. The bone cavity must be created before the prosthesis is seated or implanted, and, traditionally, a surgeon removes worn, excess, or diseased bone structure from an implant area in which the bone cavity will be formed, and then drills and hollows out the bone cavity (e.g., a bone cavity along a medullary canal of a bone of the patient). A prosthesis usually includes a stem, or other protrusion, that is inserted into the bone cavity.

To create such a bone cavity, high energy linear forces are required to impart high energy linear impacts onto one or more surgical tools. A typical technique that the surgeon uses is manually hammering a broach (e.g., a cutting tool that conforms to a shape of the stem of the prosthesis) into the implant area using a mallet. However, this manual approach presents challenges and problems, such as being imprecise, leading to unnecessary mechanical stress on the bone of the patient, and producing unsatisfactory results (e.g., a location and configuration of the bone cavity are inaccurate). Additionally, this manual approach requires the surgeon to expend significant energy creating the high energy linear forces that are required to impart the high energy linear impacts onto the broach, leading to fatigue of the surgeon.

In some cases, the surgeon uses a powered impactor for orthopedic operations that require high energy linear impacts. However, typical powered impactors have disadvantages and drawbacks, such as inefficiently communicating energy necessary to provide the high energy linear impacts (e.g., inefficiently converting rotational motional into linear motion to cause a thrown mass to move and strike an impact surface of an anvil), inadequate robustness (e.g., typical powered impactors include a relatively high number of components that wear easily and have a short life), complex and expensive construction, and having a large size and/or weight which impedes maneuverability and access to the surgical site.

For example, typical powered impactors include a power launch spring, a thrown mass, and an anvil. To provide an impact force, the power launch spring is released from a compressed state converting potential energy, stored in the power launch spring, to kinetic energy. The power launch spring transmits the kinetic energy to the thrown mass, resulting in an acceleration of the thrown mass from an initial position toward the anvil. After the thrown mass impacts the anvil, the power launch spring retracts and returns the anvil to the initial position.

However, when the power launch spring is used to launch the thrown mass, typical energy conversion efficiencies are less than 50%. Furthermore, the repetitive launching and retracting of the power launch spring during each operational cycle can lead to material fatigue causing reduced elasticity and increased wear in one or more components of the typical powered impactors and audible harmonics do to spring cycling.

Additionally, typical powered impactors inefficiently use a clutch and/or an energy storage device (e.g., a flywheel) to communicate linear motion to the thrown mass (e.g., typical powered impactors inefficiently convert rotational motion to linear motion). For example, if the thrown mass is coupled to a linear motion converter, then the clutch is used to engage the flywheel, which is powered by the motor, to the linear motion converter to convert rotational motion (e.g., generated by the flywheel) into the linear motion that causes the thrown mass to linearly move. Accordingly, each component (e.g., the motor, the energy storage device, the clutch, the linear motion converter, and the thrown mass) introduces potential failure points, which decreases robustness and increases cost of such typical powered impactors.

Furthermore, typical powered impactors have shown issues with handling axial forces communicated to an actuator (e.g., a drive motor) of the typical powered impactors. As an example, typical powered impactors cannot sufficiently mitigate axial forces (e.g., generated by high energy linear impacts provided by the typical powered impactors) such that the drive motor is damaged and/or rendered inoperable, reducing the life of the typical powered impactors and inhibiting their application in robotic surgery due to excessive recoil.

The FIGURE is a diagram of an example 100 associated with an orthopedic impactor 102. In some implementations, the orthopedic impactor 102 may be used to provide linear impacts, such as high energy linear impacts in association with orthopedic procedures, among other examples. As shown in the FIGURE, the orthopedic impactor 102 includes a motor 104, a linear motion converter 106, an anvil 108, a thrown mass 110, a controller 112, and a sensor 114.

The motor 104 may be operable to generate first rotational motion and second rotational motion (e.g. the first rotational motion and the second rotational motion may be opposite in direction, among other examples). The linear motion converter 106 may be operatively coupled to the motor 104 to convert the first rotational motion into first linear motion and the second rotational motion into second linear motion (e.g. the first linear motion and the second linear motion may be opposite in direction, among other examples).

The thrown mass 110 may be operatively coupled to the linear motion converter 106. For example, the thrown mass 110 may be operatively coupled to the linear motion converter 106 via a drive assembly and/or a gear assembly, among other examples. For example, the thrown mass 110 may move in a first linear direction (e.g., a forward linear direction) responsive to the first linear motion and may move in a second linear direction (e.g., a reverse linear direction) responsive to the second linear motion.

The anvil 108 may include at least one impact surface (e.g., shown as a first impact surface 108a and a second impact surface 108b in the FIGURE). For example, the first impact surface 108a may be associated with providing a first linear impact (e.g., in the forward direction) and the second impact surface 108b may be associated with providing a second linear impact (e.g., in the reverse direction).

In some implementations, the thrown mass 110 may be associated with a first position. For example, the first position may be located a distance away from the first impact surface 108a such that the thrown mass 110 is ready to move toward and impact the first impact surface 108a. As another example, the first position may be located a distance away from the second impact surface 108b such that the thrown mass 110 is ready to move toward and impact the second impact surface 108b.

In some implementations, such as during an operational cycle of the orthopedic impactor 102, the thrown mass 110 may accelerate, responsive to the first linear motion and from the first position, toward the anvil 108 to impact the at least one impact surface of the anvil 108 with a first kinetic energy and impart a linear impact force on the anvil 108, and the thrown mass 110 may return, responsive to the second linear motion, toward the first position with a second kinetic energy that is less than the first kinetic energy. For example, the second kinetic energy may be at least 50% less than the first kinetic energy when the thrown mass 110 is within 15 millimeters of the first position, among other examples.

In some implementations, the first kinetic energy may correspond to a kinetic energy of the thrown mass 110 when the thrown mass 110 is at a position relative to the at least one impact surface of the anvil 108 and the second kinetic energy of the thrown mass 110 may be a percentage of the first kinetic energy when the thrown mass 110 is at the position relative to the at least one impact surface of the anvil 108. For example, the first kinetic energy may correspond to a kinetic energy of the thrown mass 110 (e.g., responsive to the first linear motion) when the thrown mass 110 is 25 millimeters or less away from the first impact surface 108a and the second kinetic energy of the thrown mass 110 (responsive to the second linear motion) may be at least 40% less than the first kinetic energy (e.g., corresponding to the kinetic energy of the thrown mass 110 when the thrown mass is 25 millimeters or less way from the first impact surface 108a), among other examples.

In some implementations, a motor output power (e.g., of the motor 104) may be controlled to provide the first rotational motion and/or the second rotational motion at one or more times and/or one or more positions associated with the thrown mass 110. For example, the motor output power may be reduced to provide the second rotational motion during movement of the thrown mass 110 toward the first position, among other examples.

In some implementations, an anvil stroke (e.g., of the anvil 108) may be a distance responsive to the first kinetic energy. For example, the anvil stroke may be 18 millimeters or less responsive to the first kinetic energy, among other examples.

In some implementations, the linear motion converter may include any suitable means for converting the rotational motion to linear motion. For example, the linear motion converter may include a lead screw and lead nut assembly, a belt and pulley assembly, a chain and sprocket assembly, a rack and pinion assembly, and/or a ball screw and ball nut assembly, among other examples. In some implementations, the motor 104 and the linear motion converter 106 may operate along distinct parallel axes.

In some implementations, the sensor 114 may detect one or more parameters associated with the motor 104, the linear motion converter 106, the anvil 108 and/or the thrown mass 110. For example, the sensor 114 may include one or more position sensors, velocity sensors, acceleration sensors, force sensors, and/or or temperature sensors, among other examples. The sensor 114 may provide feedback to the controller 112 to enable closed-loop control of the motor output power and/or timing of the operational cycle, among other examples.

Accordingly, in some implementations, an orthopedic impactor (e.g., the orthopedic impactor 102) may include a motor (e.g., the motor 104) configured to generate rotational motion (e.g., in forward and reverse directions), a linear motion converter (e.g., the linear motion converter 106) operatively coupled to the motor and configured to convert the rotational motion into linear motion, a thrown mass (e.g., the thrown mass 110) operatively coupled to the linear motion converter and movable between a ready position and an impact position, and an anvil (e.g., the anvil 108) including at least one impact surface positioned to receive impact from the thrown mass, and a controller (e.g., shown as a controller 112 in the FIGURE).

In some implementations, the controller 112 may be configured to control the motor to accelerate the thrown mass from the ready position toward the impact position with a first kinetic energy magnitude, and to control the motor to return the thrown mass from the impact position toward the ready position with a second kinetic energy magnitude that is reduced relative to the first kinetic energy magnitude.

In some implementations, the reduction in kinetic energy during the return of the thrown mass reduces recoil forces transmitted through the orthopedic impactor. For example, the controller may be configured to modulate a motor output power during the return of the thrown mass (e.g. during return movement of the thrown mass) such that the second kinetic energy magnitude may be at least 50% less than the first kinetic energy magnitude, among other examples.

As indicated above, the FIGURE is provided as an example. Other examples may differ from what is described and/or shown in connection with the FIGURE. Additionally, the number and arrangement of the various components shown in the FIGURE are provided as an example.

In practice, there may be additional components, fewer components, different components, and/or differently arranged components than those described and/or shown in connection with the FIGURE. For example, the orthopedic impactor 102 may include one or more components described and/or shown in U.S. Provisional Application No. 63/863,882, filed Aug. 14, 2025, U.S. Nonprovisional application Ser. No. 19/073,013, filed Mar. 7, 2025, U.S. Provisional Application No. 63/728,398, filed Dec. 5, 2024, International Patent Application No. PCT/US2025/035879, filed Jun. 30, 2025, and/or U.S. Pat. No. 12,290,300, issued on May 6, 2025, each of which is incorporated by reference in its entirety.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. An orthopedic impactor, comprising:
   a motor operable to generate first rotational motion and second rotational motion, the first rotational motion and the second rotational motion being opposite in direction;
   a linear motion converter operatively coupled to the motor to convert the first rotational motion into first linear motion and the second rotational motion into second linear motion, the first linear motion and the second linear motion being opposite in direction;
   an anvil including at least one impact surface; and
   a thrown mass operatively coupled to the linear motion converter having a first position located a distance from the at least one impact surface,
   wherein, during an operational cycle of the orthopedic impactor:
      the thrown mass accelerates, responsive to the first linear motion and away from the first position, toward the anvil to impact the at least one impact surface with a first kinetic energy and impart a linear impact force on the anvil, and
      the thrown mass returns, responsive to the second linear motion and toward the first position, with a second kinetic energy that is less than the first kinetic energy.

2. The orthopedic impactor of claim 1, wherein the second kinetic energy is at least 50% less than the first kinetic energy when the thrown mass is within 15 millimeters of the first position.

3. The orthopedic impactor of claim 1, wherein the first kinetic energy corresponds to a kinetic energy of the thrown mass when the thrown mass is 25 millimeters or less away from the at least one impact surface and the second kinetic energy is at least 40% less than the first kinetic energy.

4. The orthopedic impactor of claim 1, wherein a motor output power is reduced to provide the second rotational motion during movement of the thrown mass toward the first position.

5. The orthopedic impactor of claim 1, wherein an anvil stroke is 18 millimeters or less responsive to the first kinetic energy.

6. The orthopedic impactor of claim 1, wherein the linear motion converter includes a lead screw and lead nut assembly.

7. The orthopedic impactor of claim 1, wherein the linear motion converter includes a belt and pulley assembly.

8. The orthopedic impactor of claim 1, wherein the linear motion converter includes a chain and sprocket assembly.

9. The orthopedic impactor of claim 1, wherein the linear motion converter includes a rack and pinion assembly.

10. The orthopedic impactor of claim 1, wherein the linear motion converter includes a ball screw and ball nut assembly.

11. The orthopedic impactor of claim 1, wherein the motor and the linear motion converter operate along distinct parallel axes.

12. An orthopedic impactor, comprising:
    a motor operable to generate rotational motion;
    a means for converting the rotational motion to linear motion;
    an anvil including at least one impact surface; and
    a thrown mass having a first position located a distance from the at least one impact surface, wherein, during an operational cycle of the orthopedic impactor:

the thrown mass accelerates, responsive to the linear motion and away from the first position, toward the anvil to impact the at least one impact surface with a first kinetic energy and impart a linear impact force on the anvil, and the thrown mass returns, responsive to the linear motion and toward the first position, with a second kinetic energy that is less than the first kinetic energy.

13. The orthopedic impactor of claim 12, wherein the second kinetic energy is at least 50% less than the first kinetic energy.

14. The orthopedic impactor of claim 12, wherein the first kinetic energy corresponds to a kinetic energy of the thrown mass when the thrown mass is 25 millimeters or less away from the at least one impact surface and the second kinetic energy is at least 40% less than the first kinetic energy.

15. The orthopedic impactor of claim 12, wherein a motor output power is reduced to provide the second rotational motion during movement of the thrown mass toward the first position.

16. The orthopedic impactor of claim 12, wherein an anvil stroke is 18 millimeters or less responsive to the first kinetic energy.

17. The orthopedic impactor of claim 12, wherein the motor and the linear motion converter operate along distinct parallel axes.

18. An orthopedic impactor, comprising:
a motor configured to generate rotational motion;
a linear motion converter operatively coupled to the motor and configured to convert the rotational motion into linear motion;
a thrown mass operatively coupled to the linear motion converter and movable between a ready position and an impact position;
an anvil including at least one impact surface positioned to receive impact from the thrown mass; and
a controller configured to:
control the motor to accelerate the thrown mass from the ready position toward the impact position with a first kinetic energy magnitude, and
control the motor to return the thrown mass from the impact position toward the ready position with a second kinetic energy magnitude that is reduced relative to the first kinetic energy magnitude.

19. The orthopedic impactor of claim 18, wherein the controller is further configured to modulate a motor output power during the return of the thrown mass such that the second kinetic energy magnitude is at least 50% less than the first kinetic energy magnitude.

* * * * *